United States Patent [19]
Ambrosio et al.

[11] Patent Number: 5,394,868
[45] Date of Patent: Mar. 7, 1995

[54] INHALATION DEVICE FOR POWDERED MEDICAMENTS

[75] Inventors: Thomas J. Ambrosio, Kendall Park; Srinivas Manthena, Bloomfield; Henry R. Sochon, Clifton, all of N.J.

[73] Assignee: Schering Corporation, Kenilworth, N.J.

[21] Appl. No.: 167,811

[22] PCT Filed: Jun. 25, 1992

[86] PCT No.: PCT/US92/05225
§ 371 Date: Dec. 16, 1993
§ 102(e) Date: Dec. 16, 1993

[51] Int. Cl.6 ............................................. A61M 15/00
[52] U.S. Cl. ............................ 128/203.15; 128/203.23
[58] Field of Search ..................... 128/203.15, 203.23, 128/203.12, 203.24; 222/345, 349, 342, 636

[56] References Cited

U.S. PATENT DOCUMENTS

| | | | |
|---|---|---|---|
| 2,581,182 | 1/1952 | Fields | 128/206 |
| 2,603,215 | 7/1952 | Arnow | 128/206 |
| 3,027,897 | 4/1962 | Carofiglio | 128/206 |
| 4,046,146 | 9/1977 | Rosskamp et al. | 128/266 |
| 4,116,195 | 9/1978 | James | 128/266 |
| 4,177,844 | 10/1978 | James | 128/266 |
| 4,240,418 | 12/1980 | Rosskamp et al. | 128/203.15 |
| 4,274,403 | 6/1981 | Struve | 128/203 |
| 4,470,412 | 9/1984 | Nowacki et al. | 128/200.18 |
| 4,524,769 | 6/1985 | Wetterlin | 128/203 |
| 4,534,345 | 8/1985 | Wetterlin | 128/203 |
| 4,570,630 | 2/1986 | Elliott et al. | 128/203.15 |
| 4,627,432 | 12/1986 | Newell et al. | 128/203 |
| 4,667,668 | 5/1987 | Wetterlin | 128/203 |
| 4,668,218 | 5/1987 | Virtanen | 604/58 |
| 4,805,811 | 2/1989 | Wetterlin | 128/203.15 |
| 4,811,731 | 3/1989 | Newell et al. | 128/203 |
| 4,907,583 | 3/1990 | Wetterlin et al. | 128/203 |
| 5,033,463 | 3/1991 | Cocozza | 128/203.21 |

FOREIGN PATENT DOCUMENTS

| | | |
|---|---|---|
| 0079478 | 5/1983 | European Pat. Off. . |
| 0424790 | 5/1991 | European Pat. Off. . |
| 4027391 | 3/1992 | Germany ................... 128/203.15 |
| 2041763 | 9/1980 | United Kingdom . |
| 2165159 | 4/1986 | United Kingdom . |
| 90123327 | 11/1990 | WIPO . |
| 9204928 | 4/1992 | WIPO ........................ 128/203.15 |

*Primary Examiner*—Edgar S. Burr
*Assistant Examiner*—Eric P. Raciti
*Attorney, Agent, or Firm*—Eric S. Dicker; John J. Maitner; Robert A. Franks

[57] ABSTRACT

A powder dispenser 10 includes a powder housing 28 for holding a supply of powdered material to be dispensed, the powder housing including a first conduit 32 extending there through in displaced relation to the powdered material; a metering plate 16 having only a single receptacle area 24 for holding a metered amount of the powdered material above a gas-permeable powder retainer 26 mounted at the metering plate, and being positioned below the powdered material, and the metering plate and the powder housing being rotatable with respect to each other so that the receptacle area is adapted to be in selective communication with the supply of powdered material or the first conduit; a base housing 48 being mounted below the metering plate and including a second conduit 52 in alignment with the first conduit at least concurrently with alignment of the receptacle area and the first conduit; a spring 62 for biasing the base housing and the powder housing toward each other; a mouthpiece 92 for enabling inhalation of the metered amount of powdered material from the receptacle area in the metering plate through the first conduit in the container, the mouthpiece being in fluid communication with the first conduit.

22 Claims, 11 Drawing Sheets

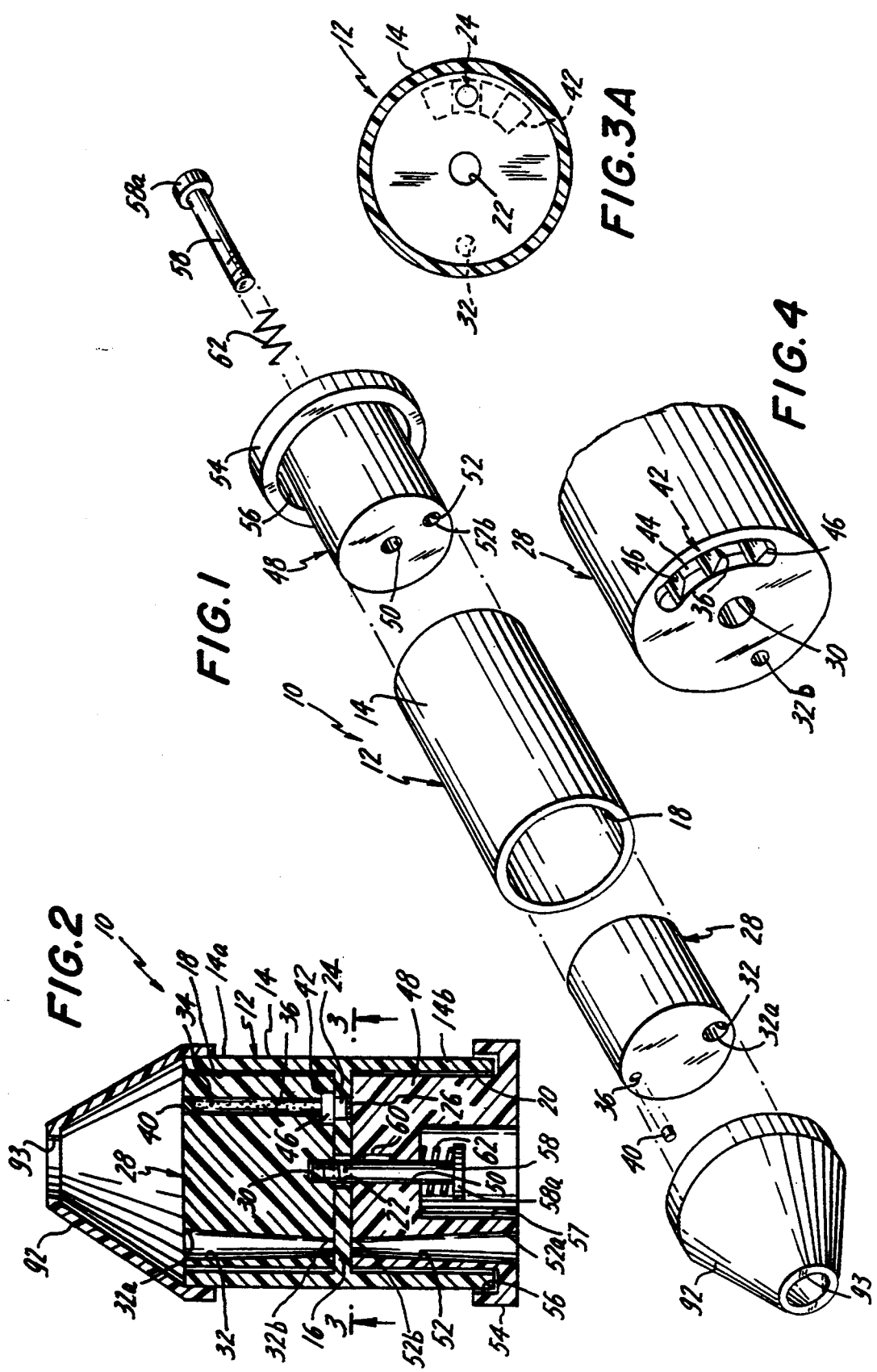

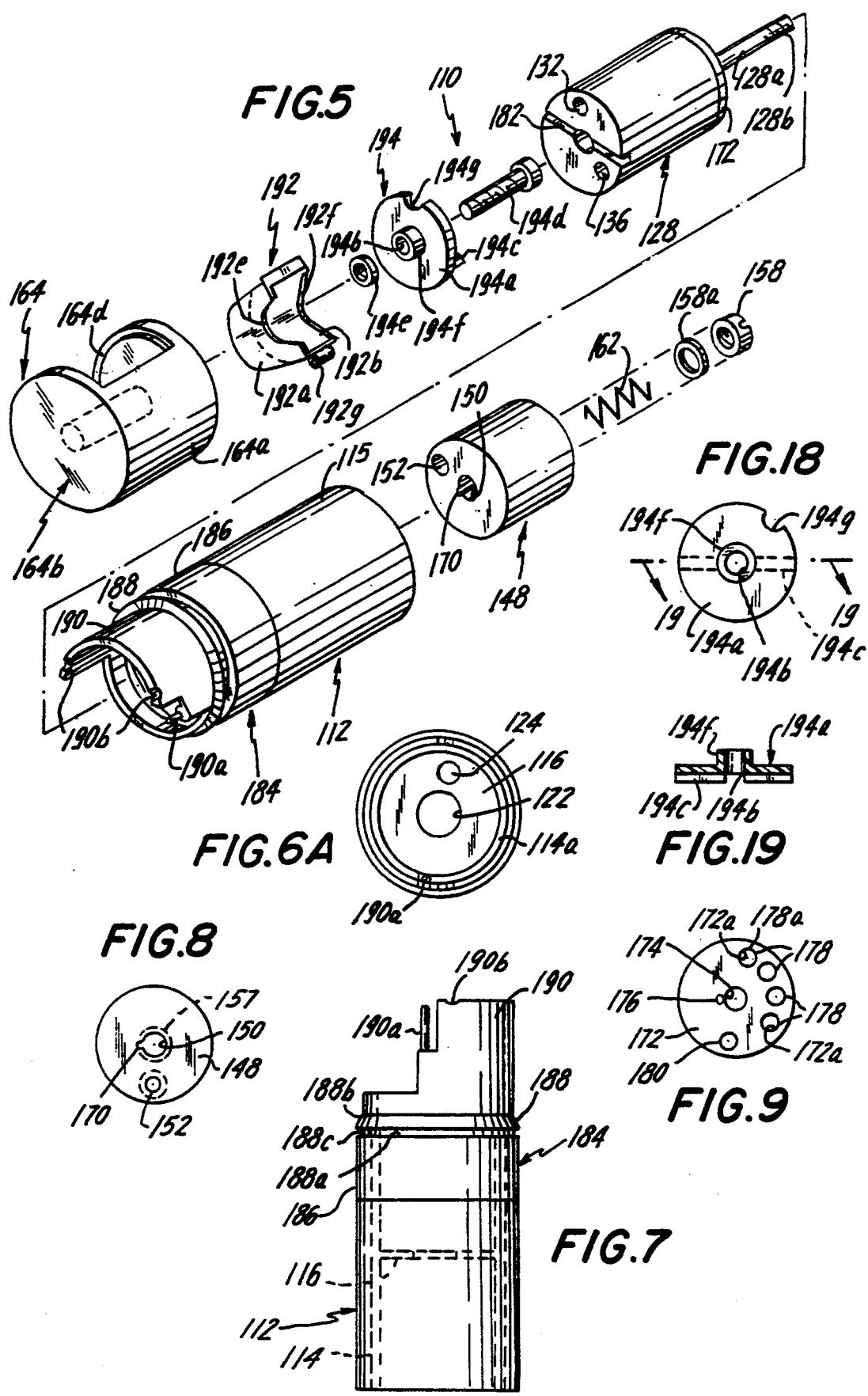

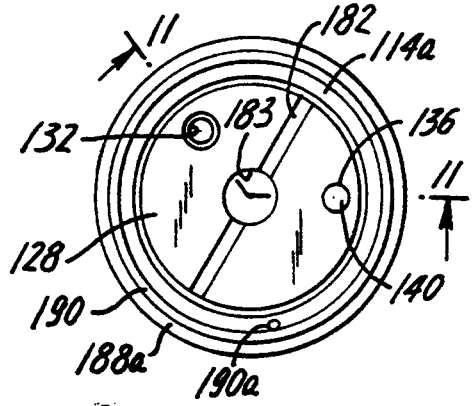
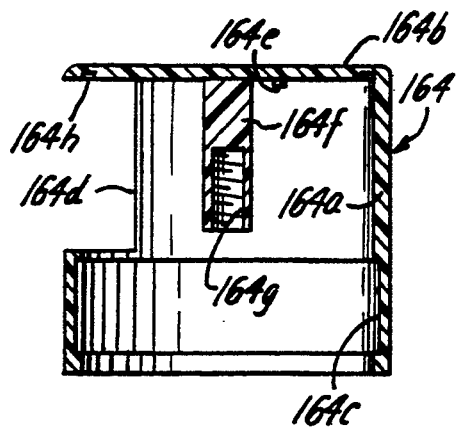
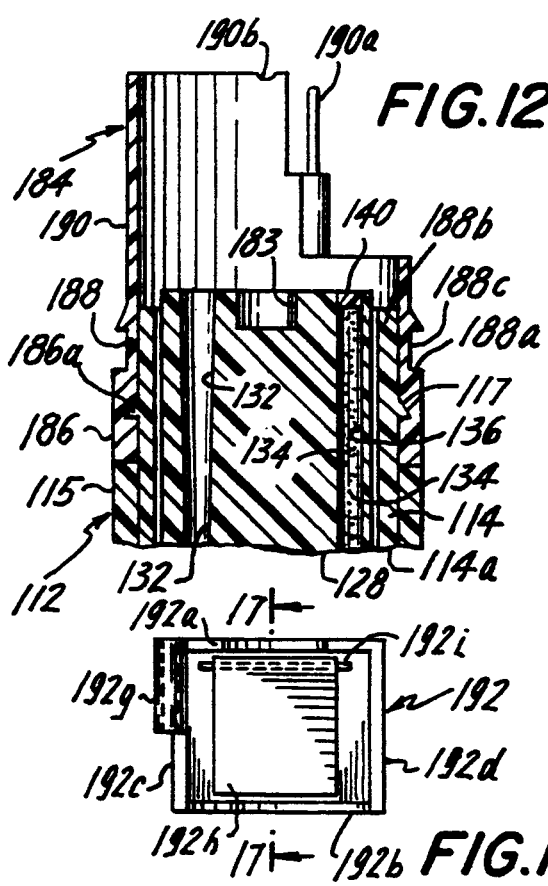
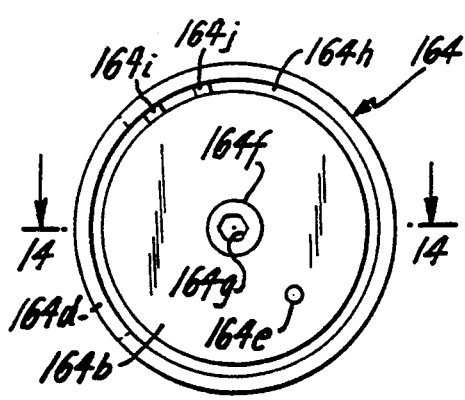
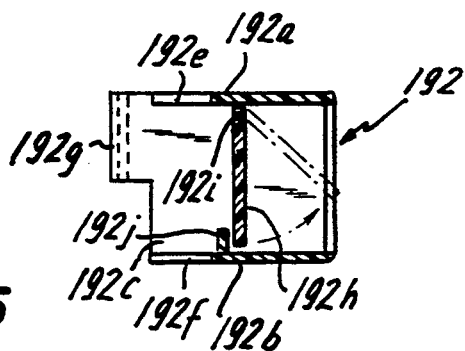
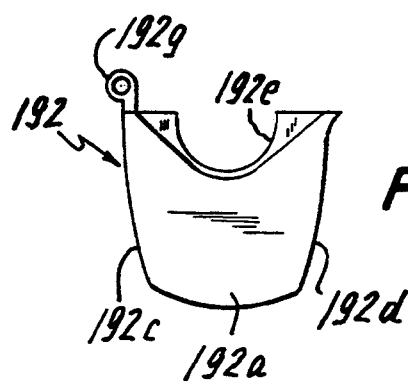

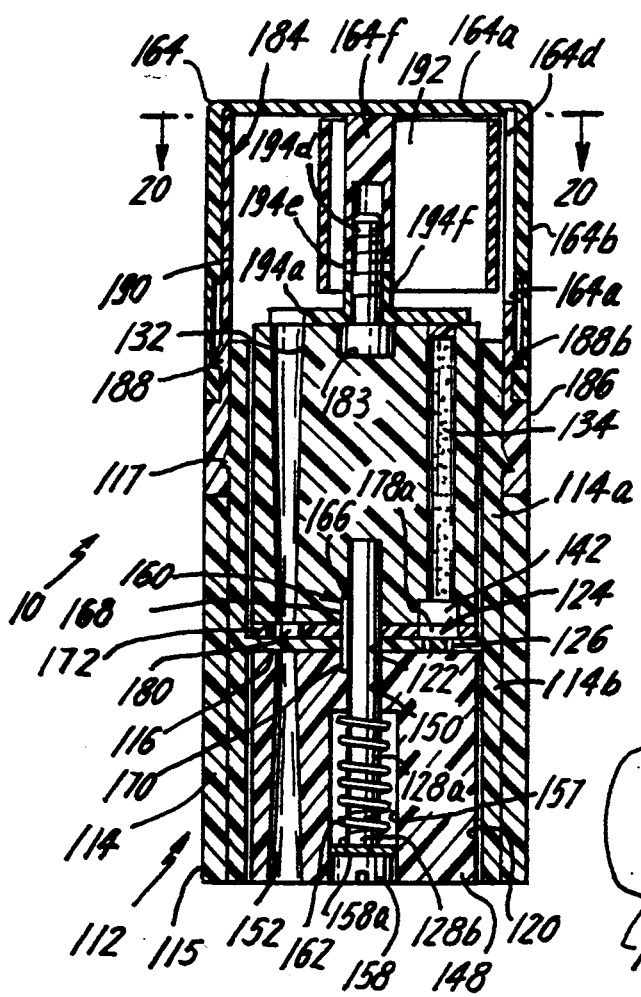
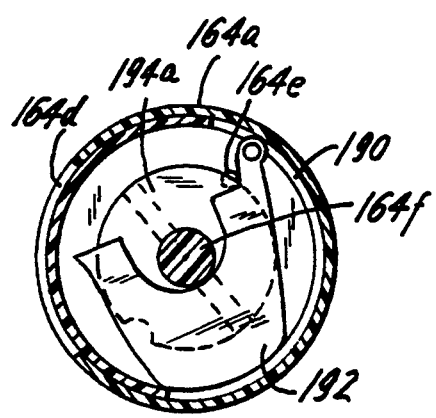
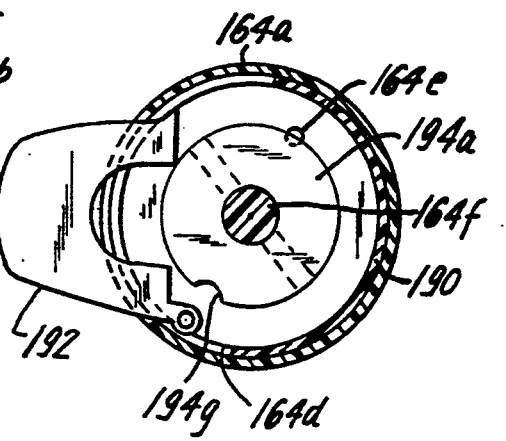
FIG.20
FIG.21
FIG.11

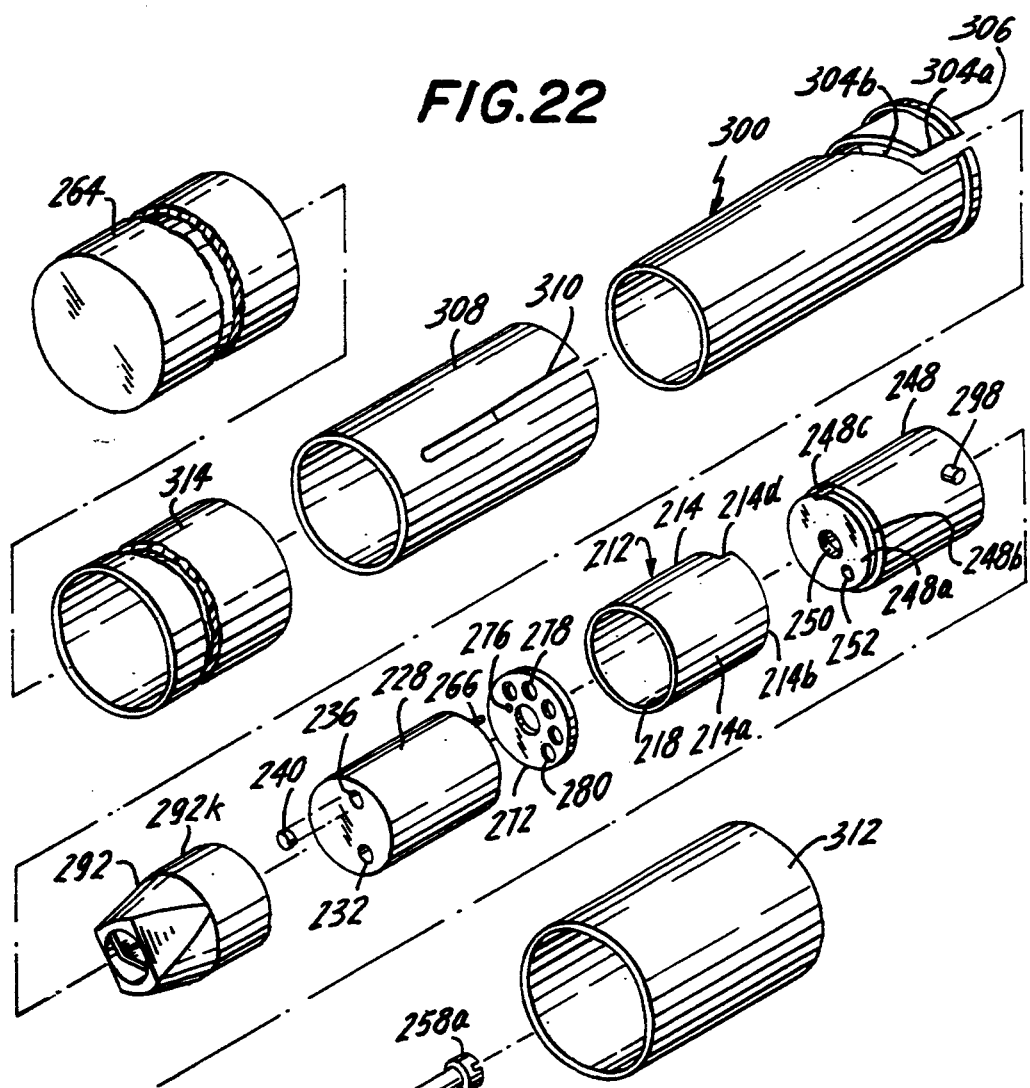
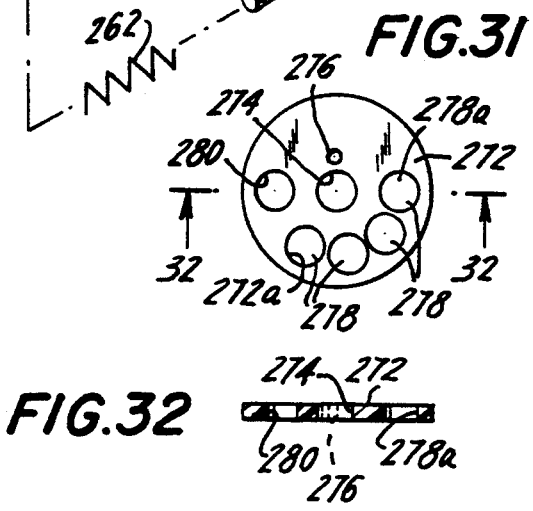
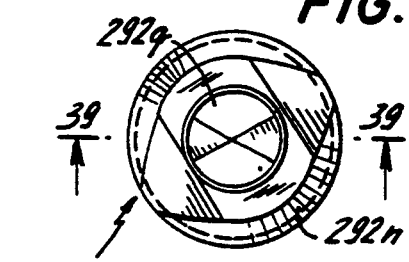

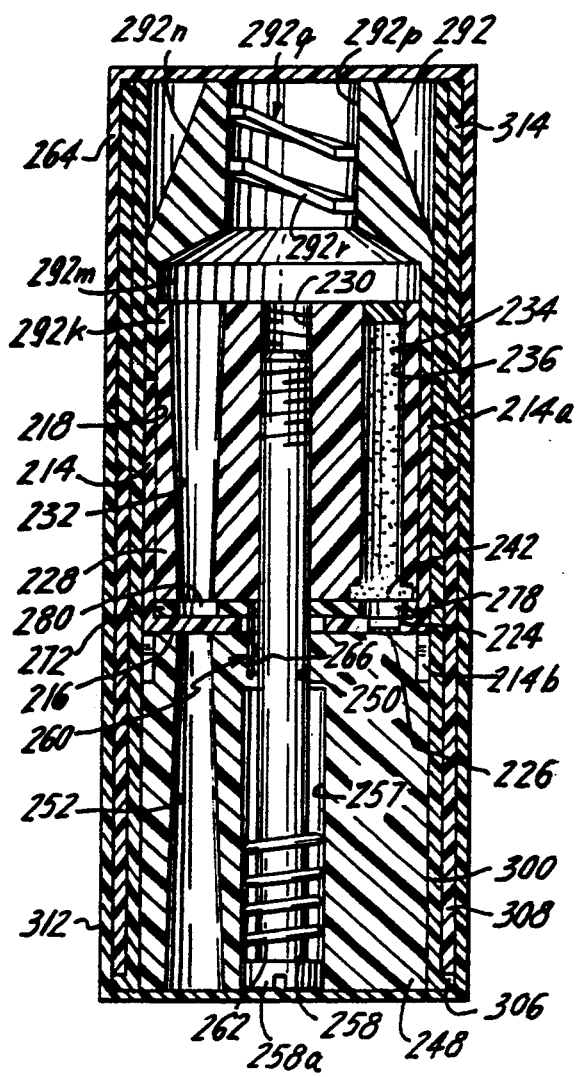
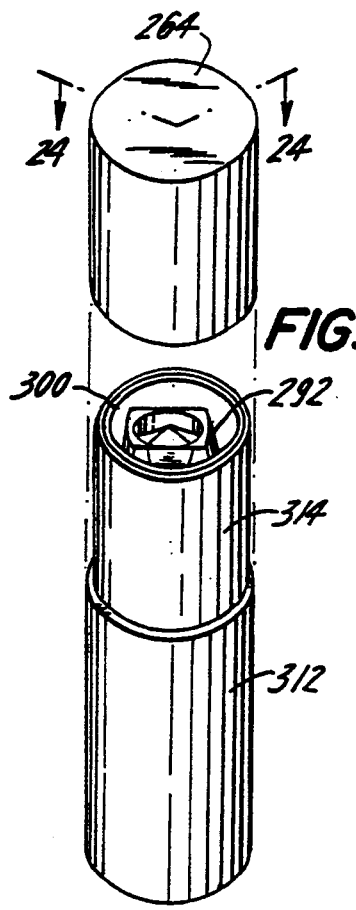
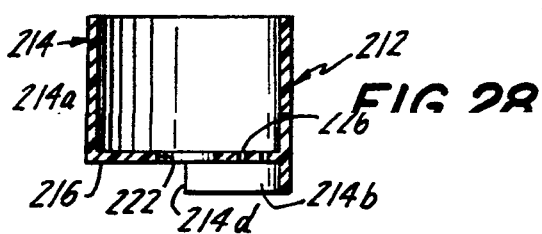
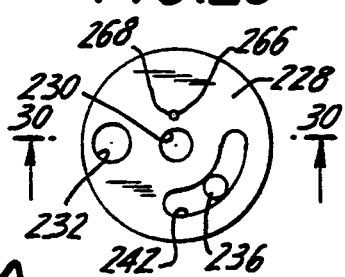
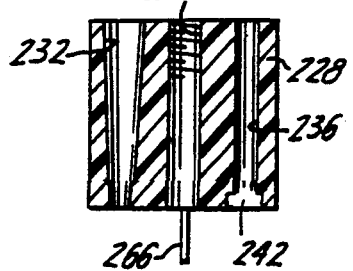

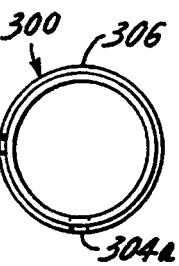
FIG. 43
FIG. 40
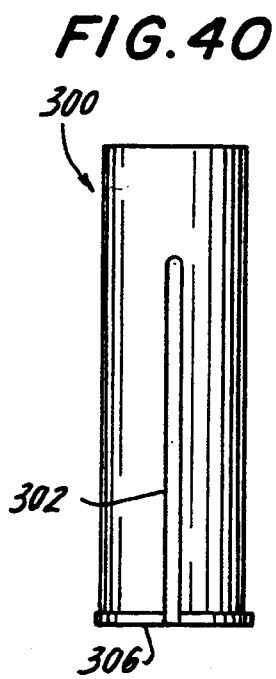
FIG. 41
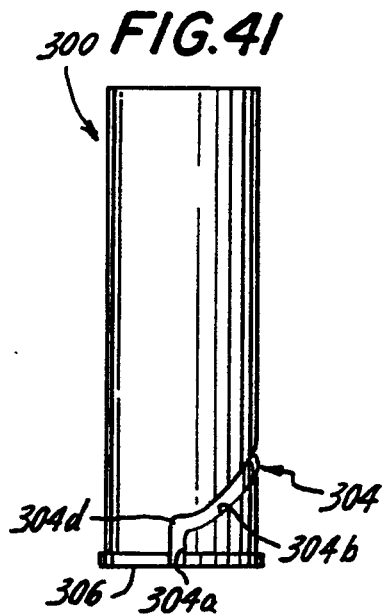
FIG. 42
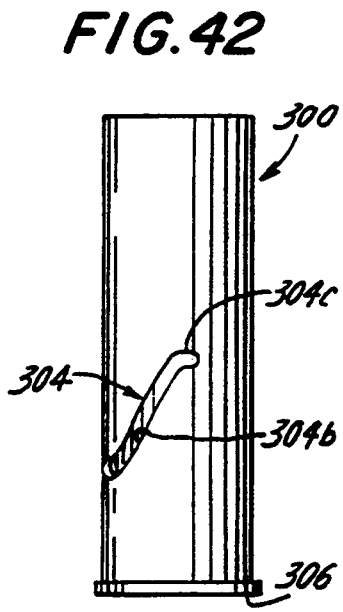
FIG. 35
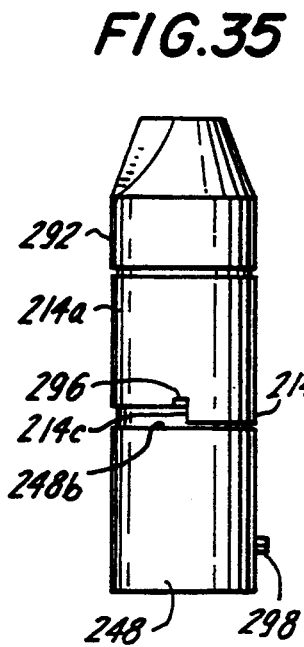
FIG. 36
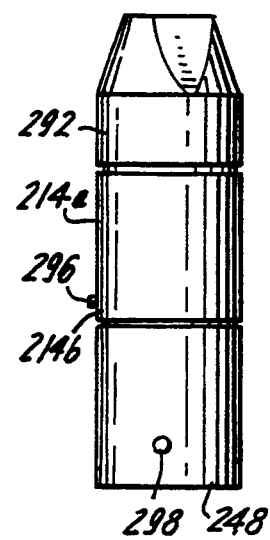
FIG. 37
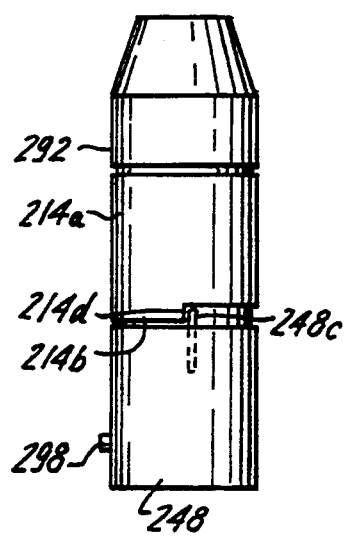

FIG. 51
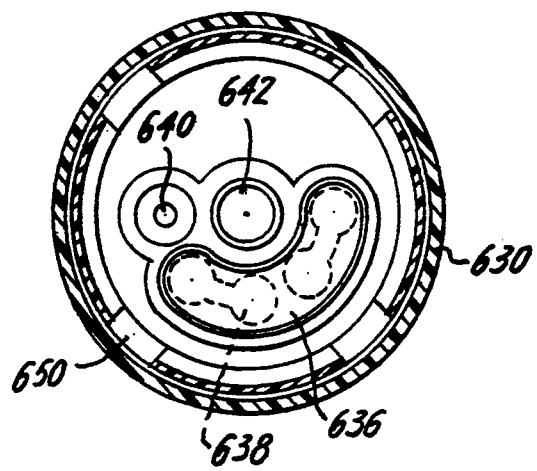
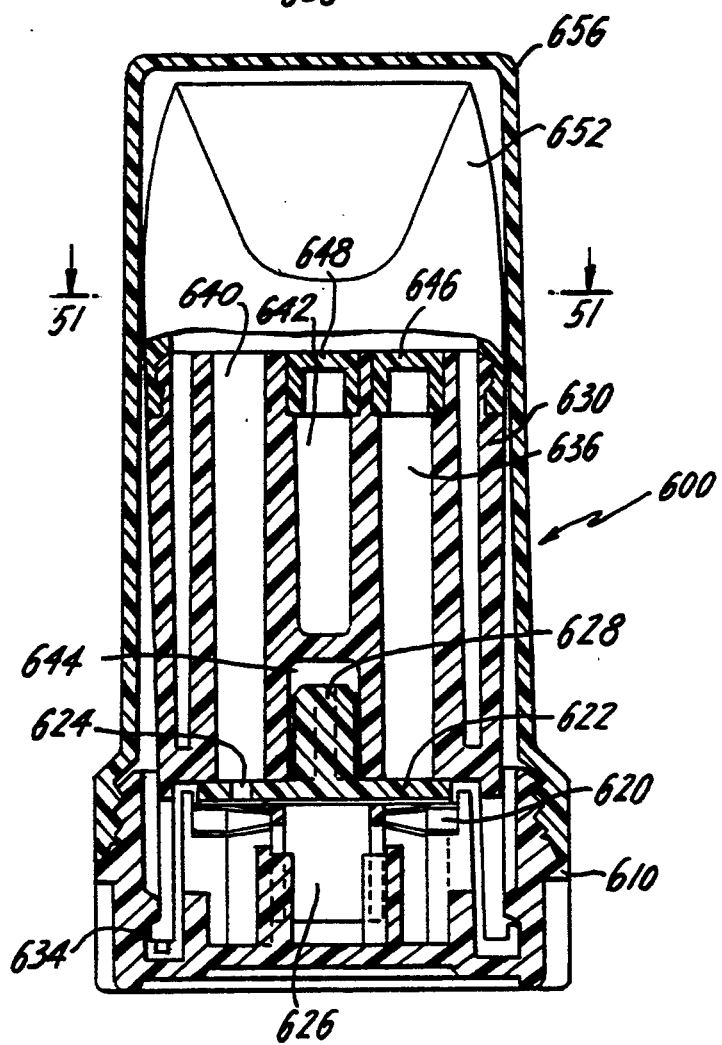
FIG. 50

INHALATION DEVICE FOR POWDERED MEDICAMENTS

INTRODUCTION TO THE INVENTION

The present invention relates generally to powder dispenser assemblies and, more particularly, is directed to a powder dispenser assembly used for inhalation of a metered dose of a powdered medicament.

When delivering medicaments, that is, pharmacologically active compounds, in solid form to the respiratory tract and to the lungs, careful attention to the accuracy of the dosage, which can be as small as 0.1 milligram, must be made. This is because such medicaments are often quite potent, and the administration of excessive amounts thereof could be harmful to the patient. Further, if the dosage that is delivered is too small, it will not serve its purpose.

It is also necessary that the particles leaving the dispenser assembly be substantially within a particular size range, since particles of the medicament which are too large may not enter the respiratory tract, but instead, will be deposited in the mouth or pharynx and thence enter the digestive tract. As an example, preferred particles can have a diameter of 1 to 5 micrometers.

Various devices have been used in order to dispense a metered dose of powdered medicament, including pressurized aerosol devices, nebulizing devices, pump inhalators and the like. With the current concern over environmental issues, however, aerosol devices, which constitute a large part of the devices now on the market, are less favored. Further, with aerosol devices, the medicament is dissolved or suspended in a liquid propellant mixture, which results in the introduction of unneeded chemical substances into the body and further adds to the complexity of the devices.

In addition to the aforementioned types of dispenser assemblies, powder dispenser assemblies are also known. Studies have shown that there are virtually no significant differences in bronchodilator responses with equivalent amounts of medicinal substances administered either by powder dispensing devices or aerosol devices. Accordingly, there is now an ever-growing demand for powder dispensing devices which can dispense metered doses of powdered medicament. With such devices, the powder is dispensed during inspiration following expiration so that there is less need to provide a synchronized release of medication with the exact start of inspiration to insure quality of the product delivery.

U.S. Pat. No. 4,524,769 to Wetterlin, the entire disclosure of which is incorporated herein by reference, describes a dosing unit that includes a storage chamber for holding the active compound, a perforated membrane rotatably positioned under the storage chamber and a holder for the membrane. Introduction of the active compound into perforations in the perforated membrane is accomplished with elastic, spring-loaded scrapers, mounted in a holder in the storage chamber. With this arrangement, the membrane is movable between a first position where active compound is introduced by the scrapers in part of the area of the perforated membrane, and a second position where the part of the area of the loaded membrane has been inserted into the air conduit in the dosage inhalator. Thus, the active compound contained in the perforations is entrained at inhalation and brought through the nozzle to the respiratory tract and the lungs of the patient.

With this arrangement, a coil spring is used to bias the scrapers into engagement with the perforated membrane. The coil spring is interposed in the storage chamber between the casing and the scraper assembly. Alternatively, it is disclosed that the coil spring can be arranged so that the membrane is pressed against the scrapers, and thereby mounted in the base or maneuvering unit. In addition to the coil spring, Wetterlin uses spring loaded pins beneath the membrane to engage the ratcheted bottom of the membrane in order to provide distinct positions for the perforated membrane when it is advanced by the base or maneuvering unit. This, of course, further complicates the construction and assembly of the device. See also U.S. Pat. Nos. 4,907,583; 4,534,345; and 4,667,668; all to Wetterlin.

U.S. Pat. No. 4,805,811 to Wetterlin discloses a dosage device which is substantially identical in all relevant respects to U.S. Pat. No. 4,524,769 to Wetterlin. With the '811 Wetterlin Patent, there is an additional funnel-like feed element positioned above the scraping unit. Also, the dosing member is provided with five recesses which are different from those described in the '769 Patent. Further, there is a spring which biases from below, unlike the '769 Patent, and the locking mechanism of the powder housing to the base housing or operating member is somewhat different.

However, with these minor differences aside, the same deficiencies found in Wetterlin '769 are found in Wetterlin '811. Thus, the devices of the Wetterlin patents all provide a relatively complicated and costly arrangement. This is the result of providing a plurality of openings in a metering plate which must be rotated separately from the main housing. Further, by providing a plurality of openings in the metering plate, a relatively complicated indexing mechanism must be provided, which is subject to breakage and which is difficult to assemble. Specifically, the Wetterlin patents require a ratchet mechanism to perform such indexing.

U.S. Pat. No. 4,668,218 to Virtanen discloses a dispenser substantially identical to the Wetterlin patents, while also providing an indicating assembly which indicates the number of medicament dosages administered.

SUMMARY OF THE INVENTION

In accordance with an aspect of the present invention, a powder dispenser includes powder housing means for holding a supply of powdered material to be dispensed, the powder housing means including a first conduit extending there through in displaced relation to the supply of powdered material; metering plate means for holding a metered amount of the powdered material, the metering plate means including only a single powder receptacle area therein for holding the metered amount of the powdered material, the metering plate means being positioned below the supply of powdered material, and the metering plate means and the powder housing means being rotatable with respect to each other so that the receptacle is adapted to be in fluid communication selectively with the supply of powdered material or the first conduit; base housing means for preventing air flow through the receptacle except when the receptacle is in alignment with the first conduit of the powder housing means, the base housing means being mounted below the metering plate means, and the base housing means including a second conduit in alignment with the first conduit of the powder housing means when the receptacle is in alignment with the first conduit of the powder housing means; spring means for biasing the base housing means and the powder housing means toward each other; and mouthpiece means for enabling inhalation of the metered amount of powdered material from the receptacle in the metering plate means through the first conduit in the container means, the mouthpiece means being in fluid communication with the first conduit.

In accordance with another aspect of the present invention, a powder dispenser further includes rotational drive means for rotating the powder housing means with respect to the metering disk means so that the first conduit is in fluid communication with the receptacle, in association with movement of the mouthpiece means to an exposed position to enable inhalation therefrom.

The above and other features of the invention will become readily apparent from the following detailed description thereof which is to be read in connection with the accompanying drawings.

BRIEF DESCRIPTION OF THE DRAWINGS

FIG. 1 is an exploded perspective view of a metered powder dose dispenser according to a first embodiment of the present invention;

FIG. 2 is a longitudinal cross-sectional view of the metered powder dose dispenser of FIG. 1 in assembled form;

FIGS. 3A and 3B are cross-sectional views of the metered powder dose dispenser of FIG. 2, taken along line 3-3 thereof;

FIG. 5 is an exploded perspective view of a metered powder dose dispenser according to a second embodiment of the present invention;

FIGS. 6A and 6B are top plan views of the assembled stationary body and cap holder of the metered powder dose dispenser of FIG. 5;

FIG. 7 is a side elevational view of the assembled stationary body and cap holder of the metered powder dose dispenser of FIG. 5;

FIG. 8 is a top plan view of the base housing of the metered powder dose dispenser of FIG. 5;

FIG. 9 is a plan view of the scraper plate of the metered powder dose dispenser of FIG. 5;

FIG. 10 is a top plan view of the assembled stationary body, cap holder and powder housing;

FIG. 11 is a longitudinal cross-sectional view of the metered powder dose dispenser of FIG. 10, with the cap thereon, taken along line 11—11 thereof;

FIG. 12 is an enlarged longitudinal cross-sectional view, similar to FIG. 11, of the upper portion of the stationary body, cap holder and powder housing;

FIG. 13 is a bottom plan view of the cap of the metered powder dose dispenser of FIG. 5;

FIG. 14 is a cross-sectional view of the cap of FIG. 12, taken along line 13—13 thereof;

FIG. 15 is a front elevational view of the mouthpiece of the metered powder dose dispenser of FIG. 5;

FIG. 16 is a top plan view of the mouthpiece of FIG. 15;

FIG. 17 is a cross-sectional view of the mouthpiece of FIG. 15, taken along line 17—17 thereof;

FIG. 18 is a top plan view of the key disk of the driver mechanism of the metered powder dose dispenser of FIG. 5;

FIG. 19 is a cross-sectional view of the key disk of FIG. 18, taken along line 19—19 thereof;

FIG. 20 is a cross-sectional view of the assembled cap, cap holder, mouthpiece and key disk of the metered powder dose dispenser of FIG. 10, taken along line 20—20 thereof;

FIG. 21 is a cross-sectional view similar to FIG. 20, with the mouthpiece extended out of the window of the cap;

FIG. 22 is an exploded perspective view of a metered powder dose dispenser according to a third embodiment of the present invention;

FIG. 23 is a perspective view of the assembled metered powder dose dispenser of FIG. 22 in the closed position, with the cap removed;

FIG. 24 is a longitudinal cross-sectional view of the metered powder dose dispenser of FIG. 23;

FIGS. 27A and 27B are top plan views of the metering disk portion of the metered powder dose dispenser of FIG. 22;

FIG. 28 is a cross-sectional view of the metering disk portion of FIG. 27, taken along line 28—28 thereof;

FIG. 29 is a bottom plan view of the powder housing of the metered powder dose dispenser of FIG. 22;

FIG. 30 is a cross-sectional view of the powder housing of FIG. 29, taken along line 30—30 thereof;

FIG. 31 is a top plan view of the scraper disk of the metered powder dose dispenser of FIG. 22;

FIG. 32 is a cross-sectional view of the scraper disk of FIG. 33, taken along line 32—32 thereof;

FIG. 35 is an elevational view of the assembled base housing, metering disk portion, scraper plate, powder housing and nozzle;

FIG. 36 is an elevational view of the assembled base housing, metering disk portion, scraper plate, powder housing and nozzle, viewed from a position 90° offset from the position of FIG. 35;

FIG. 37 is an elevational view of the assembled base housing, metering disk portion, scraper plate, powder housing and nozzle, viewed from a position 180° offset from the position of FIG. 35;

FIG. 38 is a top plan view of the nozzle of the metered powder dose dispenser of FIG. 22;

FIG. 39 is a cross-sectional view of the nozzle of FIG. 38, taken along line 39—39 thereof;

FIG. 40 is an elevational view of the guide sleeve of the metered powder dose dispenser of FIG. 22;

FIG. 41 is an elevational view of the guide sleeve of FIG. 40, viewed from a position 90° offset from the position of FIG. 40;

FIG. 42 is an elevational view of the guide sleeve of FIG. 40, viewed from a position 180° offset from the position of FIG. 40;

FIG. 43 is a top plan view of the guide sleeve of FIG. 40;

FIG. 48 is a cross-sectional view of a metered powder dose dispenser according to a fourth embodiment of the present invention;

FIG. 50 is a cross-sectional view of the assembled dispenser of FIG. 49; and

FIG. 51 is a top view of the partially assembled powder dispenser of FIG. 49.

DETAILED DESCRIPTION OF THE PREFERRED EMBODIMENTS

Figure 4B:
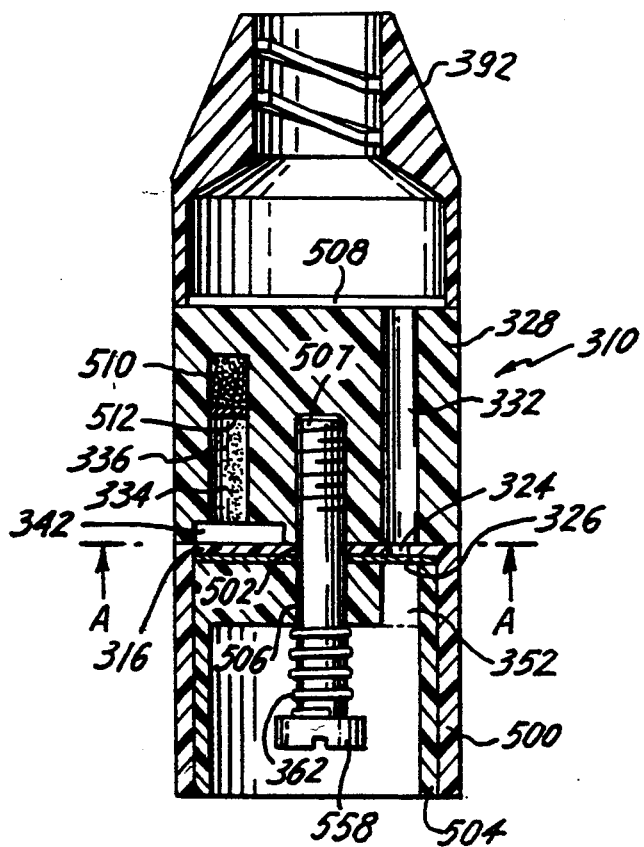
FIG. 4 is a bottom perspective view of the powder housing of the metered powder dose dispenser of FIG. 1.

Referring to the drawings in detail, and initially to FIGS. 1–4 thereof, a metered powder dose dispenser 10 according to a first embodiment of the present invention includes a stationary body 12 formed by a cylindrical wall 14 that is divided into an upper half cylindrical wall portion 14a and a lower half cylindrical wall portion 14b by a metering disk portion 16 integrally formed with cylindrical wall 14. Therefore, as shown in FIG. 2, stationary body 12 has a substantially H-configuration in the longitudinal cross-section thereof, with an upper cup-shaped recess 18 being formed between upper half cylindrical wall portion 14a and disk portion 16, and a lower cup-shaped recess 20 being formed between lower cylindrical wall portion 14b and disk portion 16.

Disk portion 16 is formed with a central opening 22, and a single powder receptacle 24 (FIG. 3A) is located near the periphery thereof. Receptacle 24 is above a gas-permeable powder retainer 26. Receptacle 24 and retainer 26 can be formed by inserting a gas permeable filter, mesh or perforated plate element, having a height less than the thickness of metering disk 16, into the lower portion of an opening of suitable dimension and shape in said metering disk; receptacle 24 will thus be formed above the element in the opening. Alternatively, powder receptacle 24 can comprise an opening in disk 16 and powder retainer 26 can comprise a covering on the lower surface of said disk, extending at least over said opening. As a further alternative, metering disk 16 is formed from a porous material and powder receptacle 24 is formed by a recess in the disk. The filter, mesh or plate element constitutes retainer 26, and preferably has a minimal restrictive effect on gas flow therethrough, while preventing appreciable loss of powdered medicament below the lower surface of metering disk 16. To maintain a constant volume of powder receptacle 24, powder retainer 26 is preferably fixedly mounted in or below the opening, such as by frictional fit, welding or use of an adhesive. A gas permeable filter, mesh or plate can be fabricated from any suitable material, including cellulosics, polymerics, metals, ceramics, glasses or composites thereof, exemplary useful materials including sintered porous plastics, porous polymer membranes, natural or synthetic woven fabrics, nonwoven synthetic fabrics and the like. More specifically, useful materials include polyester and polyolefin woven mesh, and porous membranes of polyolefins, polycarbonates, poly-tetrafluoroethylene, polyvinylidene dichloride, and mixed esters of cellulose.

Figure 3B:
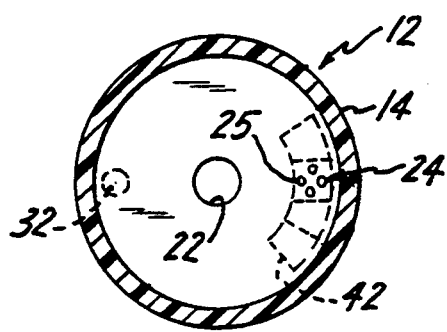

Alternatively, as shown in FIG. 3B, receptacle 24 comprises an area on disk portion 16, wherein powder is introduced into perforations 25, sized such that the powder will be retained therein until inhaled by the user. No retainer will typically be used with this configuration.

A powder housing 28 of a cylindrical configuration is positioned within upper cup-shaped recess 18. Powder housing 28 sits upon the upper surface of disk portion 16 and has an outer diameter smaller than the inner diameter of cylindrical wall 14 so as to permit relative rotation between powder housing 28 and stationary body 12. Powder housing 28 includes a central threaded opening 30 in line with central opening 22 of disk portion 16. In addition, powder housing 28 includes a first frusto-conical venturi conduit 32 extending entirely there through, substantially parallel to and offset from the central axis thereof so as to be positioned at the periphery of powder housing 28. Venturi conduit 32 has its large diameter end 32a at the upper end of powder housing 28, and its small diameter end 32b adjacent disk portion 16. In this manner, small diameter end 32b of venturi conduit 32 can be aligned with receptacle 24 to receive powdered medicaments 34 therefrom. As used herein, the terms "powdered medicaments" and "powder" include micronized powder, spheronized powder, micro-encapsulated powder, powder agglomerates and the like, and are used interchangeably with these terms herein.

In addition, powder housing 28 includes a powder supply conduit 36 positioned diametrically opposite venturi conduit 32, with the lower end of powder supply conduit 36 capable of being aligned with receptacle 24, as shown in FIG. 2. Powder supply conduit 36 is normally filled with powder 34 for inhalation, and the upper end of powder supply conduit 36 is closed by a plug 40 or the like to prevent the escape of powder from the upper end of powder supply conduit 36.

The lower end of powder supply conduit 36 exits into a manifold 42 formed in the lower surface of powder housing 28. Manifold 42 extends along an arcuate path of powder housing 28 at the periphery thereof, and is divided into chambers 44 by scraper plates 46. The upper end of at least one chamber 44 is in communication with the lower end of powder supply conduit 36, while the lower ends of all chambers are adapted to be in communication with receptacle 24 upon relative rotation between powder housing 28 and disk portion 16. Further, the lower ends of scraper plates 46 are at the same level as the lower surface of powder housing 28, and therefore, are in contact with the upper surface of disk portion 16. Accordingly, upon relative rotation between stationary body 12 and powder housing 28, powder 34 falls into at least one chamber 44 of manifold 42 from powder supply conduit 36, and then is scraped by scraper plates 46 into receptacle 24 so as to accurately and completely fill the same.

Metered powder dose dispenser 10 further includes a base housing 48 of a cylindrical configuration, positioned within lower cup-shaped recess 20. Base housing 48 also has an outer diameter smaller than the inner diameter of cylindrical wall 14 so as to permit relative rotation between base housing 48 and stationary body 12. Further, base housing 48 includes a central opening 50 in line with central opening 22 of disk portion 16. A second frusto-conical venturi conduit 52 extends entirely through base housing 48, substantially parallel to and offset from the central axis thereof, so as to be positioned at the periphery of base housing 48. Venturi conduit 52 has its large diameter end 52a at the lower end of base housing 48, and its small diameter end 52b adjacent disk portion 16. In this manner, small diameter end 52b of venturi conduit 52 can be aligned with receptacle 24, and therefore, in line with powder 34 therein. As will be described hereinafter in greater detail, base housing 48 is rotatably fixed with respect to powder housing 28 so that second venturi conduit 52 is always in alignment with first venturi conduit 32.

As shown best in FIGS. 1 and 2, base housing 48 includes an annular L-shaped lip 54 at the lower end thereof. Lip 54 defines an annular groove 56 for seating the lower end of cylindrical wall 14 therein.

Further, a central recess 57 is formed at the lower end of base housing 48, recess 57 being in fluid communication with central opening 50.

In order to rotatably lock base housing 48 to powder housing 28, a bolt 58 is inserted through central recess 57, central opening 50 and central opening 22, and threadedly received in central threaded opening 30 of powder housing 28. A conventional key-way arrangement 60 is provided in connection with central opening 50 of base housing 48 and on bolt 58 to prevent relative rotation between base housing 48 and bolt 58. As a result, relative rotation between powder housing 28 and base housing 48 is prevented, while permitting axial sliding movement there between. In other words, rotation of base housing 48 results in rotation of powder housing 28 therewith. However, base housing 48 and powder housing 28 can be moved toward and away from each other in the axial directions thereof.

It is important to the present invention that powder 34 not prematurely escape from receptacle 24, and in this regard, a coil spring 62 is positioned in central recess 57 between base housing 48 and the head 58a of bolt 58 in order to normally bias powder housing 28 and base housing 48 together in the axial directions thereof. As a result, the lower surface of powder housing 28 is in contact with the upper surface of disk portion 16, while the upper surface of base housing 48 is in contact with the lower surface of disk portion 16. In this manner, the escape of powder 34 deposited into receptacle 24 is prevented.

In addition, the large diameter end of a frusto-conical mouthpiece 92 is fixedly mounted to the upper end of powder housing 28. An opening 93 is provided in the opposite, small diameter end of mouthpiece 92.

In operation, venturi conduits 32 and 52 are initially in alignment with receptacle 24. Then, stationary body 12 and base housing 48 am rotated 180° with respect to each other to the position shown in FIG. 1. During such rotation, manifold 42 comes into communication with receptacle 24. As a result, powder 34 in chambers 44 therein is deposited in receptacle 24 and scraped thereinto by scraper plates 46. Then, with receptacle 24 filled, base housing 48 and stationary body 12 are rotated back 180° with respect to each other so that venturi conduits 32 and 52 are once again in alignment with receptacle 24. It is then only necessary for the user to inhale through opening 93 in mouthpiece 92 so that air is drawn upwardly through venturi conduit 52 and powder retainer 26, thereby carrying the powder from receptacle 24 through venturi conduit 32 and out through opening 93.

It will be appreciated that scraper plates 46 of the present invention operate to provide the scraping action during both. counterclockwise and clockwise rotation that is during both the 180° loading stage and the reverse 180° movement to the inhalation stage.

Accordingly, with the present invention, a metered powder dose dispenser 10 is provided that accurately measures the doses of powdered medicament to be delivered to the patient. Specifically, dispenser 10 is greatly simplified in construction and assembly over the prior art. This occurs by reason of the metering disk portion being integrally formed with the stationary body that rotatably holds the powder housing and base housing. Further, with the present invention, there is only a single receptacle in the metering disk portion, so as to eliminate the need for any complex ratchet assembly.

Thus, the present invention differs from the aforementioned Wetterlin patents which require a plurality of openings in a metering plate which must be rotated separately from the main housing. By providing a plurality of openings in the metering plate, a relatively complicated indexing mechanism must be provided, which is subject to breakage and which is difficult to assemble. Specifically, the Wetterlin patents require a ratchet mechanism to perform such indexing.

Referring now to FIGS. 5-21, a metered powder dose dispenser 110 according to a second embodiment of the present invention will now be described, in which elements corresponding to those of dispenser 10 of the first embodiment are denoted by the same reference numerals incremented by 100, and a detailed description of the common elements will be omitted herein for the sake of brevity.

Specifically, as shown therein, the basic mechanism of dispenser 10 is found in dispenser 110, with some variations thereof. First, instead of a bolt 58 extending into threaded engagement directly with the main body of the power housing, powder housing 128 includes a central extension shaft 128a integrally formed at the lower surface thereof. Shaft 128a extends through central opening 150 of base housing 148, into central recess 157. The free end of shaft 128a includes external threads 128b thereon and a nut 158 is threadedly engaged therewith, in order to secure powder housing 128 to base housing 148. Of course, as with dispenser 10, a coil spring 162 is positioned between base housing 148 and nut 158 in order to normally bias powder housing 128 and base housing 148 together in the axial directions thereof. In this regard, a washer 158a is interposed around shaft 128a, between nut 158 and coil spring 162. As a result, the lower surface of powder housing 128 is in contact with the upper surface of disk portion 116, while the upper surface of base housing 148 is in contact with the lower surface of disk portion 116.

Further, a key-way arrangement 160 is provided to prevent relative rotation between powder housing 128 and base housing 148, while permitting axial sliding movement there between. Specifically, key-way arrangement 160 includes a small diameter stop rod 166 secured in an opening 168 at the lower surface of powder housing 128 and extending downwardly therefrom in the axial direction of powder housing 128. A small diameter opening 70 is provided in the upper surface of base housing 148 and extends in the axial direction of base housing 148. Opening 170 is aligned with opening 168 so as to slidably receive stop rod 166 therein. As a result, rotation of powder housing 128 results in rotation of base housing 148 therewith. However, base housing 148 and powder housing 128 can be moved toward and away from each other in the axial directions thereof, because stop rod 166 can slide in the axial direction thereof within opening 170.

It will be appreciated that central opening 122 of disk portion 116 is of a sufficiently large diameter to receive stop rod 166 therein. In this manner, rotation of powder housing 128 and base housing 148 can occur with respect to disk portion 116, without interference from stop rod 166.

As another modification, manifold 142 is merely formed as an arcuate open area in communication with powder supply conduit 136. In other words, there are no scraper plates formed in manifold 142. Instead, a separate scraper disk 172 of identical outer diameter to powder housing 128, is effectively secured to the lower surface of powder housing 128 by any suitable means. For example, the central opening 174 of scraper disk 172 can be of a slightly smaller diameter than shaft 128a so that scraper disk 172 is force fit thereon. Alternatively, an adhesive or the like can be used to secure scraper disk 172 to the Tower surface of powder housing 128. Of course, scraper disk 172 includes a small diameter opening 176 for receiving stop rod 166 there through, so that scraper disk 172 is fixed in position with respect to powder housing 128.

Scraper disk 172 includes a plurality of circular holes 178 extending there through and positioned immediately under manifold 142. It will be appreciated from the discussion that follows that holes 178 need not be circular. With this arrangement, powder 134 from powder supply conduit 136 falls into manifold 142, and then into holes 178. When powder receptacle 124 (FIG. 6A) is positioned under holes 178, powder 134 therein falls into receptacle 124, above retainer 126, and is scraped thereinto by the walls 172a of scraper disk 172 that define holes 178, during relative rotation of powder housing 128 and scraper disk 172 with respect to disk portion 116. In Other words, these walls 172a function in an equivalent manner to scraper plates 46 of dispenser 10. Preferably, as shown, there are four holes 178 in alignment with manifold 142.

Figure 6B:
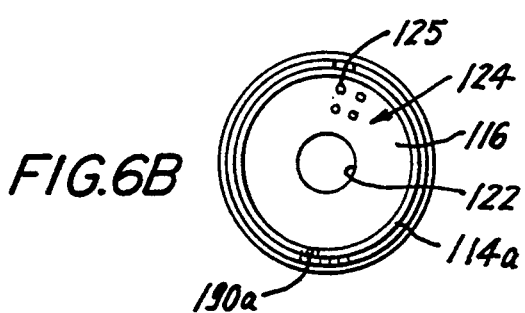
Figure 25:
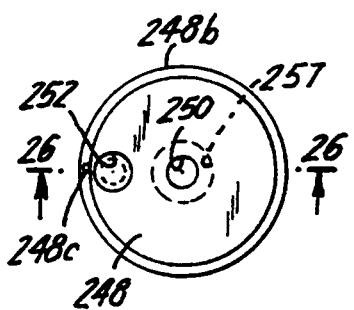
FIG. 25 is a top plain view of the base housing of the metered powder dose dispenser of FIG. 22.
Figure 26:
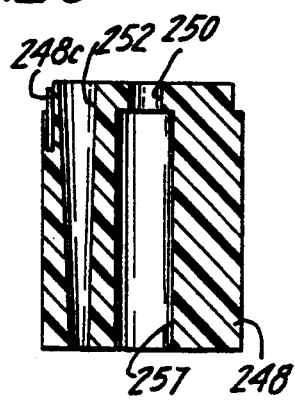
FIG. 26 is a cross-sectional view of the base housing of FIG. 25, taken along line 26—26 thereof.
Figure 46:
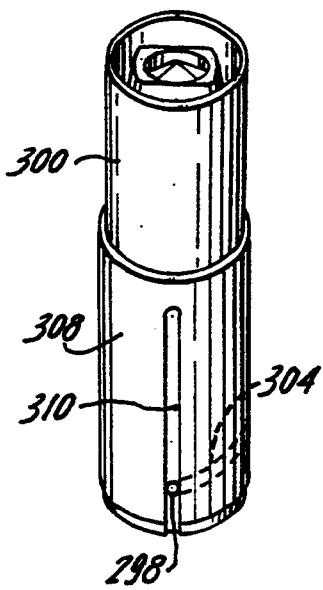
FIG. 46 is a perspective view of the assembled metered powder dose dispenser of FIG. 22, with the cap removed and without the bottom friction cap and top friction sleeve, and in the retracted position.
Figure 47:
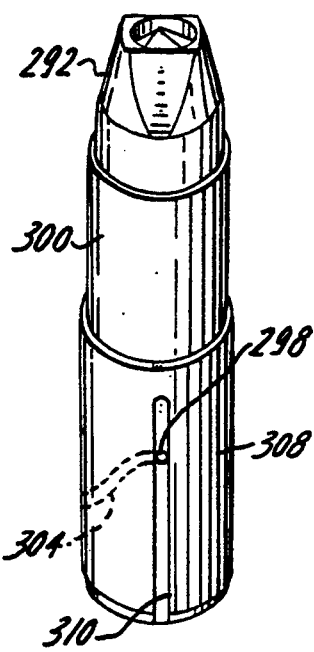
FIG. 47 is a perspective view of the assembled metered powder dose dispenser of FIG. 46, in the extended, operable position.
Figures 33, 34:
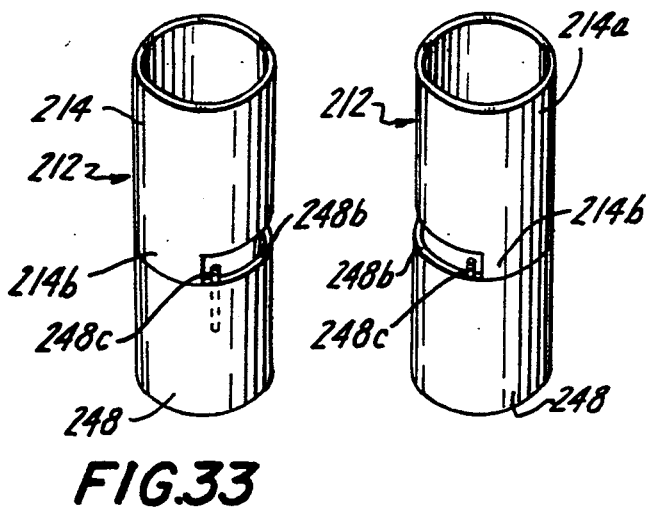
FIG. 33 is a perspective view of the assembled base housing and metering disk portion of the metered powder dose dispenser of FIG. 22.
FIG. 34 is a perspective view of the assembled base housing and metering disk portion of FIG. 33, with the metering disk portion rotated 180° with respect to the base housing from the position shown in FIG. 33.
Figure 44:
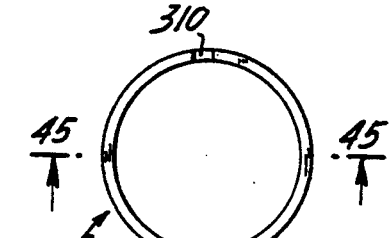
FIG. 44 is a bottom plan view of the driving sleeve of the metered powder dose dispenser of FIG. 22.
Figure 45:
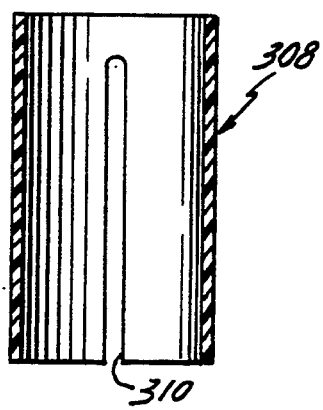
FIG. 45 is a cross-sectional view of the driving sleeve of FIG. 44, taken along line 45–45 thereof.

As shown in FIG. 6B, powder receptacle 124 can be an area comprising perforations 125. In this modification, retainer 126 may not be needed for retaining powder in the receptacle until inhalation is commenced.

In addition, there is an additional hole 180 in scraper plate 172 which is in alignment with venturi conduits 132 and 152. With this arrangement, it will be appreciated that one hole 178a is in diametrically opposite relation to hole 180. This is because manifold 142 extends past powder supply conduit 136. However, it will be appreciated that venturi conduit 132 is not diametrically opposite powder supply conduit 136, but rather, is arcuately spaced therefrom by about a 135° arc.

Further, annular L-shaped lip 54 is eliminated with dispenser 110. Accordingly, base housing 148 fits entirely within lower cup-shaped recess 120 of stationary body 12. In order to rotate powder housing 128 and base housing 148 relative to disk portion 116, powder housing 128, rather than base housing 148, is rotated by means of a diametrical driver slot 182 in the upper surface of powder housing 128, as will be described in more detail hereinafter.

A cap holder 184 is mounted in surrounding relation to upper half cylindrical wall portion 114a of stationary body 112 for holding a cap 164 of a conventional nature thereon. For example, the arrangement of cap 164 and cap holder 184 can be of the type sold by Somova S.p.A. of Milano, Italy.

Specifically, stationary body 112 has an outer sleeve 115 that surrounds lower half cylindrical wall portion 114b and approximately one-half of upper half cylindrical wall portion 114a, and is secured thereto by welding, an adhesive, a press fit or the like. The outer surface of upper half cylindrical wall portion 114a that extends above sleeve 115, is provided on the outer surface thereof with a circumferential tang 117.

Cap holder 184 includes a cylindrical gripping section 186 which is engaged over upper half cylindrical wall portion 114a and which seats on the upper edge of sleeve 115. In this regard, cylindrical gripping section 186 has an annular groove 186a in the inner wall thereof, which rides over and is engaged by circumferential tang 117 to retain cap holder 184 on stationary body 112. The lower edge of cylindrical gripping section 186 seats on the upper edge of sleeve 115 in order to position tang 117 correctly with respect to annular groove 186a. In addition, the inner diameter of gripping section 186 is slightly smaller than the outer diameter of upper half cylindrical wall portion 114a so as to retain gripping section 186 thereon with a friction fit. In this manner, cap holder 184 is generally not rotatably mounted on stationary body 112. Alternatively, a weld or an adhesive can be used.

Cylindrical gripping section 186 leads into a reduced diameter cylindrical cap securing section 188 integrally formed therewith and defining an annular shoulder 188a therewith. Cap securing section 188 is further formed with an annular tang 188b on the outer surface thereof so as to define an annular groove 188c between annular tang 188b and shoulder 188a, the purpose for which will be explained hereinafter.

Finally, cap securing section 188 leads into a substantially semi-cylindrical cap guiding section 190 integrally formed therewith and of the same diameter. One edge of cap guiding section 190 is formed with a pivot pin 190a for pivoting a mouthpiece 192 thereon, as will also be explained hereinafter. Two recesses 190b are formed at opposite ends on the upper edge of cap guiding section 190.

A cap 164 having a cylindrical outer wall 164a and a closed top wall 164b, has its lower open end rotatably mounted to cap holder 184, which in turn, as aforementioned, is fixed to the upper end of stationary body 112. The inner diameter of cylindrical outer wall 164a is similar to the outer diameter of cap securing section 188 and cap guiding section 190. Further, the inner: surface of cylindrical outer wall 164a at the lower end thereof, is formed with an annular groove 164c which receives annular tang 188b to rotatably secure cap 164 onto cap holder 184. In such position, the lower open end of cylindrical outer wall 164a seats on annular shoulder 188a.

In addition, a window 164d is cut out of cylindrical outer wall 164a, through which the aforementioned mouthpiece 192 can extend, as will be described hereinafter.

Window 164d can extend, for example, about an arc of approximately 80°.

Further, a short stop pin 164e is formed at a peripheral portion of the inner surface of top wall 164b, the purpose for which will be described hereinafter.

Cap 164 also includes a circular peripheral groove 164h in the inner surface of top wall 164b, immediately adjacent the juncture of top wall 164b with cylindrical outer wall 164a. As shown in FIG. 11, groove 164h receives the upper edge of cap guiding section 190 therein when cap 164 is assembled on cap holder 184. Two closely spaced ridges 164i and 164j are formed in groove 164h so as to receive recesses 190b on cap guiding section 190 at the extreme rotatable positions of cap 164 in order to releasably lock cap 164 at those positions.

A mouthpiece 192 is positioned within cap 164 and is pivotally connected on pivot pin 190a of cap guiding section 190. As shown, mouthpiece 192 is formed by two substantially parallel top and bottom walls 192a and 192b, and two side walls 192c and 192d which connect together top and bottom walls 192a and 192b, and which slightly converge toward each other at the forward ends thereof. Further, the rear portions of top and bottom walls 192a and 192b are formed with arcuate cut-outs 192e and 192f, respectively. This is because top wall 164b has central shaft 164f extending down therefrom, so that it is necessary to provide cut-outs 192e and 192f in order to pivot mouthpiece 192 about shaft 164f, between its retracted position totally within cap 164 (FIG. 20) and its extended position out through window 164d (FIG. 21 ). Shaft 164f has an internally threaded opening 164g at its lower end.

In order to pivotally connect mouthpiece 192 within cap 164, mouthpiece 192 is formed with a cylindrical pivot pin holder 192g connected across the rear edge of side wall 192c, near the upper end thereof. Thus, pivot pin holder 192g receives pivot pin 190a in order to pivotally mount mouthpiece 192 on pivot pin 190a within cap 164.

As will be appreciated from the discussion which follows, when manifold 142 is in communication with powder receptacle 124, mouthpiece 192 is pivoted to a retracted position within cap 164, and when venturi conduits 132 and 152 are in communication with powder receptacle 124, mouthpiece 192 is pivoted to an extended position out of window 164d. In the extended position, the user can inhale through mouthpiece 192 to receive the medicament powder 134 held in receptacle 124.

In many instances, however, the user will feel a need to exhale into mouthpiece 192 immediately after inhaling powder 134. In other words, the user may exhale before removing his mouth from mouthpiece 192. Accordingly, moisture from the user's mouth would be supplied back to receptacle 124. In order to prevent this occurrence, a flap 192h is pivotally mounted at its upper end by a pivot rod 192i, within mouthpiece 192. Specifically, pivot rod 192i extends across the upper ends of side walls 192c and 192d, approximately mid-way along the length thereof, in order to pivotally mount flap 192h therein. A stop 192j is fixed to bottom wall 192b behind flap 192h in order to prevent pivoting of flap 192h rearwardly and inwardly, while permitting pivoting of flap 192h outwardly. In this manner, when the user inhales, flap 192h pivots outwardly and upwardly to permit passage of the micronized powder 134, as shown by the dashed lines in FIG. 17. Once the user stops inhaling, flap 192h falls by gravity back to its blocking position with respect to the opening through mouthpiece 192. If the user exhales while his mouth is still on mouthpiece 192, flap 192h is prevented from further pivoting inwardly by stop 192j. As a result, no moisture from such exhalation reaches receptacle 124.

Unlike dispenser 10 in which base housing 128 is rotated relative to disk portion 16, powder housing 128 and base housing 148 of dispenser 110 are rotated relative to disk portion 116 by rotating powder housing 128. This is accomplished by rotating cap 164 relative to stationary body 112.

Specifically, rotation means 194 is mounted to cap 164 for rotating powder housing 128. Rotation means 194 includes a key disk 194a having a central hole 194b and a diametrical driving key 194c at the lower end thereof. A central cylindrical boss 194f can also be provided on the opposite surface of key disk 194a. A bolt 194d extends through hole 194b and the aligned boss 194f, and is threadedly engaged within internally threaded opening 164g of shaft 164f, in order to secure key disk 194a to cap 164. Of course, other means of securing key disk 194a to cap shaft 164f can be provided, such as a press fit, weld or the like. It will be appreciated, as shown, that key disk 194a, when secured to cap 164, is positioned below the lower surface of bottom wall 192b of mouthpiece 192. In order to accurately position key disk 194a, a spacer 194e can be provided between key disk 194a and the lower end of shaft 164f. In this position, key disk 194a is fixed in position to cap 164. Thus, driving key 194c engages within diametrical driver slot 182 in the upper surface of powder housing 128 when key disk 194a is assembled with cap 164. Accordingly, when cap 164 is rotated on cap holder 184, driving key 194c of key disk 194a, which is engaged within driver slot 182, causes rotation of powder housing 128 therewith. Since stationary body 112 is held stationary by the user, this results in relative rotation of powder housing 128 and base housing 148 relative to stationary body 112. In addition, key disk 194a is provided with a peripheral cut-out 194g which aligns with the upper end of venturi tube 132 when driving key 194c is engaged within driver slot 182. In this manner, when venturi tube 132 is in alignment with powder openings 126, key disk 194a will not block the passage of powder from venturi tube 132 to mouthpiece 192.

In addition, it will be appreciated that a central bore 183 is formed in the upper surface of powder housing 128 so as to receive the head of bolt 194d when driving key 194c of key disk 194a is engaged within driver slot 182.

In general operation of mouthpiece 192, when hole 178a and manifold 142 are in alignment with powder receptacle 124, mouthpiece 192 is positioned entirely within cap 164. In such position, the rear edge of top wall 192a at the juncture with pivot pin holder 192g, is in contact with stop pin 164e of cap 164. This prevents further rotation of cap 164 on cap holder 184. In this position, it will be appreciated that semi-cylindrical cap guiding section 190 covers window 164d to prevent access to mouthpiece 192 during non-use.

As cap 164 is rotated, powder housing 128 is also rotated therewith. As a result, walls 172a scrape powder 134 into receptacle 124. After 180° of travel of powder housing 128 and base housing 148 relative to disk portion 116, venturi conduits 132 and 152, and hole 180, are in alignment with receptacle 124. During this rotation, side wall 192c hits against an edge defining window 164d. Upon continued rotation of cap 164 toward the position where venturi conduits 132 and 152 are in alignment with receptacle 124, this edge of window 164d, which is stationary, forces mouthpiece 192 out of window 164d, that is, to the only place that mouthpiece 192 can move while permitting continued rotation of cap 164. Mouthpiece 192 therefore pivots outwardly about pivot pin 190a. Because the rear edges of side walls 192c and 192d are spaced apart a greater distance than the width of window 164d, mouthpiece 192 can only extend out of window 164d a predetermined amount, which limits the rotation of cap 164 to a fixed position. This fixed position corresponds to the alignment of venturi conduits 132 and 152, and hole 180, with receptacle 124. The user then merely inhales through mouthpiece 192 to receive powder 134 contained within receptacle 124.

In addition to the aforementioned advantages achieved with dispenser 10, it will be appreciated that dispenser 110 provides additional advantages. Specifically, the mechanism for rotating the powder housing relative to the metering disk is associated with movement of the mouthpiece between its retracted and exposed positions, and therefore provides a dual function in a simplified manner. Also, because of flap 192h, moisture from exhalation is prevented from entering through mouthpiece 192.

Referring now to FIGS. 22–47, a metered powder dose dispenser 210 according to a third embodiment of the present invention will now be described, in which elements corresponding to those of dispenser 110 of the second embodiment are denoted by the same reference numerals incremented by 100, and a detailed description of the common elements will be omitted herein for the sake of brevity.

Specifically, as shown therein, the basic mechanism of dispenser 110 is found in dispenser 210, with some variations thereof. In particular, the arrangement of powder housing 228, base housing 248, disk portion 216 and scraper plate 272 is virtually unchanged from the corresponding counterparts in dispenser 110, with the following exceptions.

In the first place, there is only an upper half cylindrical wall portion 214a to stationary body 212, so that upper half cylindrical wall portion 214a and disk portion 216 effectively have a cup-shaped configuration which defines an upper cup-shaped recess 218 that receives powder housing 228 therein. In place of the lower half cylindrical wall portion, there is provided a semi-cylindrical flange 214b of a small height, with flange 214b being formed as an extension of upper half cylindrical wall portion 214a on the opposite side of disk portion 216. Because flange 214b has a semi-cylindrical configuration, flange 214b thereby includes two opposite stop edges 214c and 214d which function to limit rotation of powder housing 228 and base housing 248 with respect to disk portion 216, as will be described in greater detail hereinafter.

The upper end of base housing 248 is cut-away to form a reduced diameter cylindrical upper end 248a that defines an annular shoulder 248b upon which the lower end of flange 214b sits. An axially oriented stop pin 248c is fixed within the periphery of base housing 248, and thereby does not increase the outer diameter thereof. Stop pin 248c extends upwardly in the axial direction of base housing 248, and is exposed immediately above annular shoulder 248b. As a result, in the assembled condition, stop pin 248c extends between stop edges 214c and 214d of flange 214b. During operation, when powder housing 228 and base housing 248 are rotated relative to stationary body 212, stop pin 248c will hit against either stop edge 214c or stop edge 214d to limit rotation of powder housing 228 to 180°. These extreme positions of rotation will correspond to a first position in which venturi conduits 232 and 252, and hole 280, are in alignment with powder receptacle 224, above powder retainer 226, and a second position in which powder supply conduit 236, manifold 242 and holes 278 are in alignment with receptacle 224.

Figure 27B:
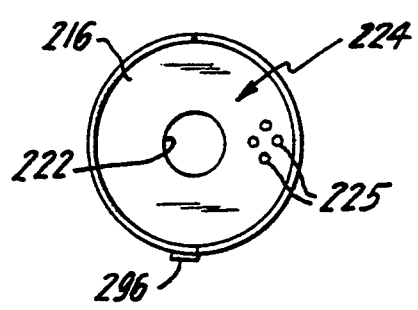

As with the other dispenser, configurations shown herein, powder receptacle 224 can comprise an opening (FIG. 27A) having powder retainer 226 beneath, or can comprise an area containing perforations 225 (FIG. 27B).

Unlike dispenser 110, powder housing 228 and base housing 248 of dispenser 210 are connected together in a similar manner to dispenser 10 of the first embodiment. Specifically, in order to rotatably lock base housing 248 to powder housing 228, a bolt 258 is inserted through central recess 257 and central opening 250 of base housing 248, central opening 222 of metering disk portion 216 and central opening 274 of scraper disk 272, and threadedly received in central threaded opening 230 of powder housing 228. Further, a coil spring 262 is positioned in central recess 257 between base housing 248 and the head 258a of bolt 258 in order to normally bias powder housing 228 and base housing 248 together in the axial directions thereof. As a result, the lower surface of scraper disk 272, which is positioned below powder housing 228, is in contact with the upper surface of disk portion 216, while the upper surface of base housing 248 is in contact with the lower surface of disk portion 216.

There is also a similar key-way arrangement 260 to that of dispenser 110, with a stop rod 266, opening 268 in powder housing 228, and a small diameter opening 270 in base housing 248.

In addition, a mouthpiece 292 is fixedly mounted to the upper end of powder housing 228. Specifically, mouthpiece 292 has a cylindrical securement section 292k which is secured over the upper end of powder housing 228 with a friction fit, a weld, an adhesive or the like. Cylindrical securement section 292k forms a chamber 292m which is in fluid communication with the upper end of venturi conduit 232. A frusto-conical inhalation section 292n has its greater diameter end formed integrally with the upper end of cylindrical section 292k. Frustoconical inhalation section 292n has a central axial bore 292p formed entirely there through and which is in fluid communication with chamber 292m. In this manner, a user can inhale powder 234 through venturi conduit 232, chamber 292m and bore 292p, when venturi conduits 232 and 252 are in alignment with receptacle 224. The entire mouthpiece 292 is preferably of a one-piece molded plastic construction.

A deflecting portion 292q of mouthpiece 292 includes a plurality of, for example two, helical vanes 292r secured within bore 292p of inhalation section 292n, in the manner taught in U.S. Pat. No. 4,907,583 to Wetterlin. Helical vanes 292r deflect the powder particles so as to dash the same against the inner wall of inhalation section 292p by centrifugal force, whereby large particles or particle aggregates are shattered into small particles, and also, the particles collide with each other which results in a mutual grinding or shattering action between the particles.

The major difference between dispensers 110 and 210 is the manner in which disk portion 216 is rotated with respect to powder housing 228 and base housing 248, which will now be described.

A first pin projection 296 is formed on the periphery of disk portion 216, and extends radially outward therefrom. Preferably, pin projection 296 is formed immediately above stop edge 214c of flange 214b. A second pin projection 298 is formed on the periphery of base housing 248 near the lower end thereof, and extends radially outward therefrom to a length of approximately twice the radial length of first pin projection 296. Second pin projection 298 is approximately 90° offset from first pin projection 296 when stop pin 248c abuts either stop edge 214c or 214d. Specifically, when stop pin 248c abuts stop edge 214d, second pin projection 298 is in line with the center of flange 214b.

In order to engage pin projections 296 and 298 to rotate disk portion 216 relative to powder housing 228 and base housing 248, a cylindrical guide sleeve 300 extends over the entire assembly so far described, that is, sleeve 300 extends over base housing 248, stationary body 212 and mouthpiece 292. Guide sleeve 300 includes an axially oriented slot 302 being open at the lower edge of guide sleeve 300 and extending approximately 76% of the height of guide sleeve 300. Slot 302 is adapted to receive first pin projection 296. In this regard, the radial length of first pin projection 296 is such that the outer extent of first pin projection 296 does not extend farther than the outside diameter of guide sleeve 300. By this arrangement, guide sleeve 300 is effectively locked to disk portion 216 so that disk portion 216 is prevented from rotating relative to guide sleeve 300, but is permitted to move axially with respect thereto, by means of first pin projection 296 in slot 302.

In addition, guide sleeve 300 includes a helical slot 304. Specifically, helical slot 304 includes an axially oriented lead-in portion 304a, which is open at the lower edge of guide sleeve 300 and extends approximately 10% of the height of guide sleeve 300. Lead-in portion 304a is angularly offset from slot 302 by approximately 90°. Lead-in portion 304a leads into a helical portion 304b, which extends helically upward in a direction away from slot 302 to a position approximately diametrically opposite lead-in portion 304a and axially offset from lead-in portion 304a. The juncture 304d of lead-in portion 304a and helical portion 304b corresponds to the position of second pin projection 298 therein when guide sleeve 300 is assembled over base housing 248, stationary body 212 and mouthpiece 292. The height of helical portion 304b from its lead-in end to its termination end is approximately 29% of the height of guide sleeve 300. Finally, helical portion 304b terminates in a termination portion 304c which is oriented transverse to lead-in portion 304a and which extends in a direction away from helical portion 304b.

As an example of dimensions that can be used, guide sleeve 300 can have a height of 2.625 inches, axially oriented slot 302 can have a height of 2 inches, lead-in portion 304a can have a height of 0.25 inch, and helical portion 304b can have a height of 0.75 inch.

Helical slot 304 receives second pin projection 298 therein when guide sleeve 300 is inserted over base housing 248, stationary body 212 and mouthpiece 292. In this manner, if guide sleeve 300 is held stationary, rotation of second pin projection 298 will cause second pin projection 298 to ride within helical portion 304b. As a result, base housing 248 will rotate with respect to disk portion 216 which is held fixed by first pin projection 296 in slot 302 of guide sleeve 300. In this manner, receptacle 224 will move from a position in alignment with manifold 242 to a position in alignment with venturi conduits 232 and 252 so that the user can inhale powder 234.

At the same time, it will be appreciated that movement of second pin projection 296 will cause base housing 248 to move axially upward with respect to guide sleeve 300. As a result, the entire arrangement of base housing 248, stationary body 212 and mouthpiece 292 will move upwardly. Since slot 302 is axially oriented, disk portion 216 will still be fixed against rotation, but will move upwardly since first pin projection 296 is positioned within slot 302. During this upward movement, mouthpiece 292 will be rotated with base housing 248 and powder housing 228, and will also be moved upwardly out of guide sleeve 300. In this regard, mouthpiece 292 will be exposed to the user when receptacle 224 is in alignment with venturi conduits 232 and 252. It will be appreciated that second pin projection 298 seats within termination portion 304c at this position to maintain mouthpiece 292 in this extended position, until the user provides a reverse rotation of second pin projection 298.

Guide sleeve 300 further includes a lower annular lip 306 extending outwardly therefrom, and slot 302 and lead-in portion 304a extend through lip 306.

In order to provide the aforementioned rotation of second pin projection 298, a cylindrical driving sleeve 308 rotatably fits over a lower portion of guide sleeve 300 and sits upon lower annular lip 306. Driving sleeve 308 includes an axially oriented slot 310, open at the lower edge of driving sleeve 308 and extending approximately the entire height of driving sleeve 300. For example, driving sleeve 308 can have a height of 1.5 inches, with slot 310 having a height of 1.25 inches. In this regard, driving sleeve 308 is slightly greater than one-half of the height of guide sleeve 300. Slot 310 receives second pin projection 298 when driving sleeve 308 is assembled on guide sleeve 300. Since the radial length of first pin projection 296 is such that the outer extent of first pin projection 296 does not extend farther than the outside diameter of guide sleeve 300, first pin projection 296 will not interfere with the rotation of driving sleeve 308 over guide sleeve 300. However, by this arrangement, driving sleeve 308 is connected with second pin projection 298 so that rotation of driving sleeve 308 will result in rotation of second pin projection 298 within helical slot 306, while also permitting the aforementioned axial movement of second pin projection 298.

A bottom friction cap 312 of the same height as driving sleeve 308 is frictionally engaged over driving sleeve 308. Bottom friction cap 312 performs a two-fold function. First, bottom friction cap 312 covers slot 310 of driving sleeve 308 and second pin projection 298. Secondly, bottom friction cap 312 ensures a positive hold of second pin projection 298 in slot 310, that is, bottom friction cap 312 prevents the side walls which define slot 310 from separating further by the force of second pin projection 298 there against during the rotating force applied thereto. In this manner, when the user grasps and rotates bottom friction cap 312, driving sleeve 308 which is frictionally engaged therewith is also rotated, thereby functioning to rotate second pin projection 298.

A top friction sleeve 314 is inserted over the remaining upper end of guide sleeve 300, and is of the same diameter as driving sleeve 308. Top friction sleeve 314 frictionally engages the upper end of guide sleeve 300. In this manner, when the user grasps and rotates top friction sleeve 314 relative to bottom friction cap 312, rotation of powder housing 228 and base housing 248 occurs relative to disk portion 216, in the manner previously discussed in detail.

Lastly, a cover cap 264 is removably inserted over top friction sleeve 314 to cover the upper open end of mouthpiece 292 when not in use. In order to use dispenser 210, the user merely removes cover cap 264, and rotates bottom friction cap 312 relative to top friction sleeve 314 to align filled receptacle 224 with venturi conduits 232 and 252.

Dispenser 210 has the same advantages of dispenser 10, as aforementioned. In addition, as with dispenser 110, the mechanism for rotating powder housing 228 relative to metering disk 216 is associated with movement of mouthpiece 292 between its retracted and exposed positions, and therefore provides a dual function in a simplified manner.

Another embodiment of the powder dispenser of the present invention is now explained with reference to FIG. 48, wherein elements corresponding to those of dispenser 210 of the third embodiment are denoted by the same reference numbers, incremented by 100; a detailed description of the common elements will be omitted herein for the sake of brevity.

Dispenser 310 comprises, beginning at the lowermost portion of the drawing, hollow cylindrical lower housing 500 provided with a flat upper termination which functions as metering plate 316, the upper termination being provided with a central opening 502 and a powder receptacle opening 324 near the periphery of the plate. Beneath the metering plate is a gas-permeable powder retainer 326; for reasons which will become apparent, only that portion of retainer 326 which lies directly beneath opening 324 must be gas-permeable but, for ease of fabrication, the entire retainer may comprise a gas-permeable material. Support 504 is disposed beneath powder retainer 326 and is provided with a central opening 506 and an opening 352 near the periphery which constitutes an air conduit. The support 504 is fixedly mounted to housing 500, such that the central openings of these components are aligned and opening 324 will align with opening 352.

Powder housing 328 is cylindrical and generally closed, being provided with a threaded opening in the lower portion thereof 507 for receiving bolt 558 and an opening 332 near the periphery which constitutes an air conduit. Contained within the powder housing is powder supply conduit 336, filled with a desired amount of powder 334, and manifold 342 which is constructed and performs substantially as previously described for manifolds 42 and 142. The powder housing may be provided with a lip 508, and the lower surface of the housing is biased against metering plate 316 of lower housing 500 by spring 362, when bolt 558 is tightened.

Mouthpiece 392, which is constructed and functions similarly to previously described mouthpiece 292, is attached to powder housing 328. Attachment may be accomplished by frictional or snap fit with lip 508 of the powder housing, alternatively by threaded engagement with the powder housing, or by equivalent means, it being preferred to occasionally detach the mouthpiece for cleaning.

It will be appreciated that the portion of dispenser 310 which is above line A—A is rotatable independently of the portion below the line. For convenience of operation, stop means (not shown) may be provided to limit the angle of relative rotation. In operation, rotation is effected to align powder receptacle 324 with manifold 342, whereupon the receptacle becomes filled with powder 334; further rotation is effected to align receptacle 324 with conduit 332, so that inhalation through mouthpiece 392 will result in a measured dose of powder being entrained in the inhaled air.

The embodiment shown in FIG. 48 has the advantage of a minimized number of components, permitting ease of manufacture and a decreased possibility of equipment malfunction before the powder supply has been depleted. Further enhancements may be provided without unduly complicating the manufacturing process, such as providing a chamber in the powder housing for holding a desiccating substance in vapor communication with the powder supply conduit; this may comprise an extension of powder supply conduit 336, which extension is filled with desiccant 510 (such as silica gel) and provided with a vapor-permeable plug or membrane 512 to prevent contamination of the medicament powder with desiccant. As in previously described embodiments, it may be desirable to provide cover caps over the mouthpiece and/or the lower housing for hygienic reasons during periods of nonuse.

Figure 49:
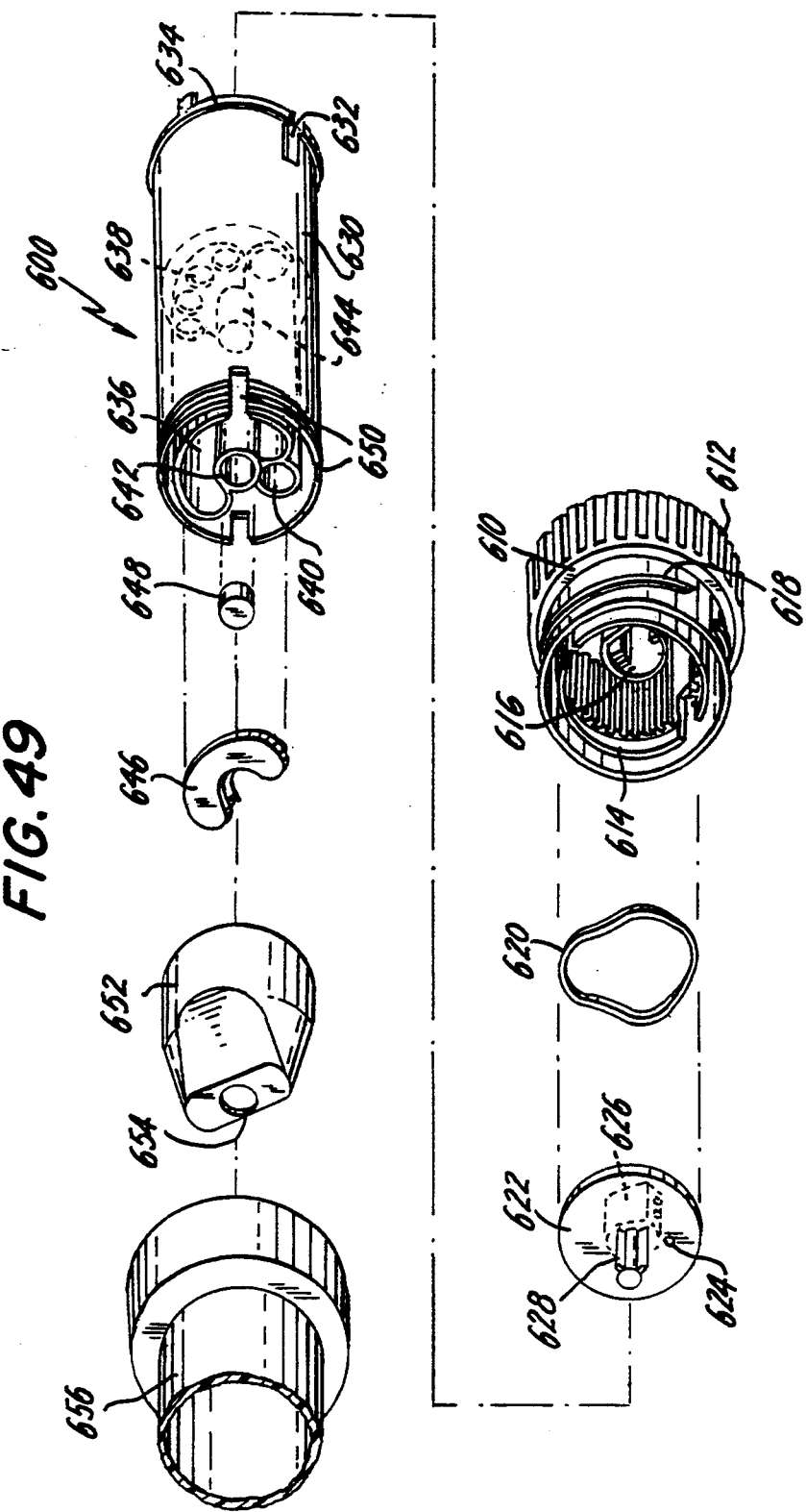
FIG. 49 is an exploded perspective view of a metered powder dose dispenser according to a fifth embodiment of the invention.

A further embodiment is shown in FIGS. 49–51, as an example of a device which is readily fabricated using a minimum number of components, and is easily assembled:

FIG. 49 is an exploded view of powder inhaler 600 depicting base unit 610 having a plurality of optional knurls 612 around its lower exterior and threads 618 around its upper exterior. Keyed opening 616 is preferably centered about the central axis of the base unit and retaining ledge 614, adapted to receive a lower surface of spring means 620 (shown as a wave spring), is disposed about an upper area of the base unit.

Motoring plate 622 is seated in the interior of the base unit above the spring means, with lower projection 626 interacting with keyed opening 616 of the base unit to ;ensure simultaneous rotation of the base unit and motoring plate. Powder receptacle 624 is located in the metering plate, and is constructed as described for other embodiments of the invention. An upper projection 628 is provided, centered about the central axis of the metering plate, and may comprise a solid post or a lobate form, or any other desired shape.

Powder housing 630 is a generally hollow tubular shell having air openings 632 at the lower edge and a ridge 634, which is adapted to provide a snap fit into a suitable groove (not shown in this figure) inside a lower portion of base unit 610. Powder reservoir 636 extends over an upper inner portion of the powder housing and is provided with manifold openings 638 at its lower termination which preferably is a flat surface, in contact with an upper surface of metering plate 622 when the device is assembled. Inhalation conduit 640 is adjacent to, and coextensive in length with, powder reservoir 636; the design is such that relative rotation of base unit 610 and powder housing 630 can selectively align powder receptacle 624 with either manifold openings 638 for filling with powder, or inhalation conduit 640 for dispensing a previously metered powder dose. Central opening 642 may be provided for receiving a desiccant material, and is located above recess 644 which can receive Upper projection 628 of metering plate 622, for proper component alignment. Plug means 646 is provided for closing powder reservior 636, and plugging means 648 is provided for closing opening 642; permeable substances are preferably used to facilitate vapor communication between the powder reservoir and the central opening. Powder housing 630 is preferably provided with supplementary air openings 650 to reduce the effort required for inhalation through the device.

Mouthpiece 652, having inhalation opening 654 in fluid communication with inhalation conduit 640, is attached to powder housing 630 by any desired means. Preferably, the mouthpiece is detachable for cleaning.

Cover 656, of which only a lower portion is shown, has an internally threaded lower area(threads not shown), which engages with threads 618 of base unit 610 to enclose the device during periods of nonuse.

FIG. 50 is a cross-sectional view of the assembled, previously described, components, except that mouthpiece 652 is shown in a partial side view.

FIG. 51 is a top view, looking downward from line 51-51, with cover 656, mouthpiece 652, plug means 646 and plugging means 648 removed. This more clearly shows manifold openings 638, located in the lower termination of powder reservoir 636.

For the convenience and safety of users, this device may also incorporate stop means for limiting relative rotation of base unit 610 and powder housing 630 to a predetermined angle. Also, it may be desirable to incorporate means for producing an audible signal such as a "click" sound at the rotational limits, so that a user will know when rotation has been correctly accomplished. A further, frequently desirable safety feature is a counter or other indicating mechanism to warn the user of impending powder depletion.

If a desiccant is required to protect the medicament against moisture contamination, the device must have a cap which prevents the entry of moisture between uses. Otherwise, desiccant capacity may be reached before all doses contained within the device are dispensed.

All of the foregoing dispensers may be fabricated from readily available materials, such as plastics, metals and the like. Typically, the various components which do not require porosity or other special properties will be molded from one or more thermoplastic substances having the desired rigidity and strength. In some embodiments, the component containing the powder receptacle is relatively thin and, to maintain a required degree of surface flatness, should be constructed from a less easily deformed substance such as a reinforced plastic, ceramic or metal. Of course, materials selected must be chemically compatible with the medication to be dispensed. For reasons of cost, a maximum utilization of plastics will be preferred where the device is intended to be disposable with no, or only a limited number of, medicament refills after the initial charge has been dispensed.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A powder dispenser comprising:
    powder housing means holding a supply of powdered material to be dispensed, said powder housing means including a first conduit extending therethrough in displaced relation to said supply of powdered material;
    metering plate means holding a metered amount of said powdered material, said metering plate means including only a single receptacle area therein for holding said metered amount of said powdered material, said metering plate means being positioned below said supply of powdered material, and said metering plate means and said powder housing means being rotatable with respect to each other so that said single receptacle area is adapted to be in fluid communication selectively with said supply of powdered material or said first conduit;
    base housing means disposed below said metering plate means and including a second conduit in alignment with said first conduit when said receptacle area is in alignment with said first conduit;
    spring means for biasing said base housing means and said powder housing means toward each other; and
    mouthpiece means for enabling inhalation of said metered amount of powdered material from said single receptacle area in said metering plate means through the first conduit in said powder housing means, said mouthpiece means being in fluid communication with said first conduit.

2. A powder dispenser according to claim 1, wherein said powder housing means has a generally cylindrical configuration with a central axis, and said first conduit extends substantially axially therethrough at a position radially offset from said central axis and substantially parallel thereto.

3. A powder dispenser according to claim 1, wherein said single receptacle area of said metering plate means is formed by a plurality of perforations which retain powder therein until said powder is dispensed.

4. A powder dispenser according to claim 1, wherein said metering plate means comprises an upper termination of said base housing means.

5. A powder dispenser according to claim 1, wherein said metering plate means comprises a gas-permeable material, and said single receptacle area comprises a recess in said metering plate means.

6. A powder dispenser according to claim 1, further including rotation limiting means for limiting rotation of said powder housing means relative to said metering disk means to an incremental angle of rotation.

7. A powder dispenser according to claim 1, further including rotational drive means for rotating said powder housing means with respect to said metering disk means so that said first conduit is in fluid communication with said receptacle area, in association with movement of said mouthpiece means to an exposed position to enable inhalation therefrom.

8. A powder dispenser according to claim 1, wherein said powder housing is bi-directionally rotatable with respect to said metering disk means between a first position in which said single receptacle area is in fluid communication with said supply of powdered material and a second position in which said single receptacle area is in fluid communication with said first conduit.

9. A powder dispenser according to claim 1, further including scraper means for scraping said powdered material into said single receptacle area during relative rotation of said metering plate means and said powder housing means, said scraper means being positioned between said supply of powdered material and said metering plate means.

10. A powder dispenser according to claim 9, wherein said scraper means includes a scraper plate having a plurality of holes therein, said scraper plate being interposed between said supply of powdered material and said single receptacle area.

11. A powder dispenser according to claim 10, further including means for rotatably fixing said scraper plate with said powder housing means.

12. A powder dispenser according to claim 1, wherein said single receptacle area of said metering plate means is formed by a gas-permeable filter, mesh or perforated plate element located at a lower portion of an opening provided in said metering plate means, said element having a height less than the thickness of said metering plate means.

13. A powder dispenser according to claim 1, wherein said single receptacle area of said metering plate means is formed by a gas-permeable filter, mesh or perforated plate element contacting a lower surface of said metering plate means and covering an opening which defines said receptacle area.

14. A powder dispenser according to claim 1, further including cylindrical wall means for holding said metering plate means in rotatable relation to said powder housing means.

15. A powder dispenser according to claim 14, further including securement means for rotatably fixing said powder housing means with said base housing means, while permitting axial movement there between.

16. A powder dispenser according to claim 1, further including moisture barrier means for preventing moisture from exhalation from passing into the dispenser through the mouthpiece means.

17. A powder dispenser according to claim 16, wherein said moisture barrier means includes a flap pivotally mounted in said mouthpiece means only for opening movement during inhalation.

18. A powder dispenser assembly according to claim 1, wherein said powder housing means further includes a third conduit therein for holding said supply of powdered material.

19. A powder dispenser according to claim 18, wherein said powder housing means has a generally cylindrical configuration with a central axis, and said third conduit extends substantially axially therethrough at a position radially offset from said central axis and substantially parallel thereto.

20. A powder dispenser according to claim 18, wherein said powder housing means further includes manifold means for supplying the powdered material from said third conduit to said single receptacle area.

21. A powder dispenser according to claim 20, further including scraper means for scraping said powdered material into said single receptacle area during relative rotation of said metering plate means and said powder housing means, said scraper means being positioned in said manifold means.

22. A powder dispenser according to claim 21, wherein said scraper means includes at least one scraper plate arranged in said manifold means, each said scraper plate having a lower edge extending as far as a lower surface of said powder housing means.

* * * * *

UNITED STATES PATENT AND TRADEMARK OFFICE
CERTIFICATE OF CORRECTION

PATENT NO. : 5,394,868
DATED : March 7, 1995
INVENTOR(S) : Thomas J. Ambrosio, et. al.

It is certified that error appears in the above-indentified patent and that said Letters Patent is hereby corrected as shown below:

Column 1, line 4, insert the following: The present application is the is the United States national application corresponding to International Application No. PCT/US92/105225. filed June 25, 1992 and designating the United States, which PCT application is in turn a continuation-in-part of U.S. No. 721,051, filed June 26, 1991 and U.S. Application Ser. No. 747,174, filed Aug. 19, 1991, both abandoned.--

Signed and Sealed this

First Day of August, 1995

Attest:

BRUCE LEHMAN

*Attesting Officer*  *Commissioner of Patents and Trademarks*